US012558273B2

(12) United States Patent
Isaac

(10) Patent No.: US 12,558,273 B2
(45) Date of Patent: Feb. 24, 2026

(54) BREATHABLE ABSORBENT ARTICLE

(71) Applicant: Allegiance Corporation, Dublin, OH (US)

(72) Inventor: Walter H. Isaac, Brimfield, MA (US)

(73) Assignee: ALLEGIANCE CORPORATION

( * ) Notice: Subject to any disclaimer, the term of this patent is extended or adjusted under 35 U.S.C. 154(b) by 824 days.

(21) Appl. No.: 17/027,349

(22) Filed: Sep. 21, 2020

(65) Prior Publication Data

US 2021/0085536 A1 Mar. 25, 2021

Related U.S. Application Data

(60) Provisional application No. 62/903,477, filed on Sep. 20, 2019.

(51) Int. Cl.
| | |
|---|---|
| *A61F 13/15* | (2006.01) |
| *A61F 13/511* | (2006.01) |
| *A61F 13/514* | (2006.01) |
| *A61F 13/53* | (2006.01) |

(52) U.S. Cl.
CPC ........ *A61F 13/53* (2013.01); *A61F 13/15203* (2013.01); *A61F 13/15577* (2013.01); *A61F 13/511* (2013.01); *A61F 13/514* (2013.01); *A61F 2013/15878* (2013.01); *A61F 2013/15959* (2013.01); *A61F 2013/15967* (2013.01); *A61F 2013/51452* (2013.01); *A61F 2013/530029* (2013.01); *A61F 2013/530051* (2013.01)

(58) Field of Classification Search
CPC ................ A61F 13/53; A61F 13/15203; A61F 13/15577; A61F 13/511; A61F 13/514;
A61F 2013/15878; A61F 2013/15959; A61F 2013/15967; A61F 2013/51452; A61F 2013/530029; A61F 2013/530051; A61F 2013/530481; A61F 13/51401; A61F 13/51405; A61F 13/51458; A61F 13/51478; A61F 2013/15056; A61F 2013/15073; A61F 2013/15284; A61F 2013/15552; A61F 2013/51441; A61F 2013/51443; A61F 2013/51447; A61F 2013/5145
See application file for complete search history.

(56) References Cited

U.S. PATENT DOCUMENTS

| | | | | |
|---|---|---|---|---|
| 5,879,341 A | * | 3/1999 | Odorzynski | ...... A61F 13/51462 604/367 |
| 6,217,890 B1 | | 4/2001 | Paul et al. | |
| 6,296,862 B1 | | 10/2001 | Paul et al. | |

(Continued)

OTHER PUBLICATIONS

Rachel Williamson et al., "Linen Usage Impact on Pressure and Microclimate Management", www.hill-rom.com, Jan. 21, 2009.

(Continued)

*Primary Examiner* — Catharine L Anderson
(74) *Attorney, Agent, or Firm* — Cardinal Health and Arent Fox LLP

(57) ABSTRACT

An absorbent article including a non-woven substrate of one or more layers of meltblown fibers and a first layer of spunbond fibers and a second layer of spunbond fibers. The absorbent article further includes an absorbent core comprising at least one of fibers or a superabsorbent polymer. At least one of the non-woven substrate or the absorbent may be treated with an alcohol repellency ("AR") treatment.

19 Claims, 6 Drawing Sheets

(56)  References Cited

U.S. PATENT DOCUMENTS

| | | | | |
|---|---|---|---|---|
| 8,454,990 | B2 * | 6/2013 | Canada ............... | A61F 13/0223 |
| | | | | 424/445 |
| 10,101,289 | B2 * | 10/2018 | Goenka ................ | G01N 27/048 |
| 10,517,778 | B2 * | 12/2019 | Wildeman ............ | A61F 13/627 |
| 12,042,364 | B2 * | 7/2024 | Wimalasena ........... | A61F 13/49 |
| 2014/0273689 | A1 * | 9/2014 | Carroll ................ | D06N 3/0011 |
| | | | | 442/123 |

OTHER PUBLICATIONS

Reifenhauser Reicofil, Reicofil Technology, URL: https://www.reicofil.com/system/uploads/attachment/file/5b8d40b659d9e61349375466/Brochure Reicofil Portfolio.pdf, Retrieved Sep. 21, 2020.

* cited by examiner

Dead Weight Hard Surface Underpad Strike Through Testing

| Sample ID | Product Description | Strike Through Testing Pressure PSI | Testing Pressure in Water Column Height (cms) | Strike Through Pass / Fail | Comment | 7.5x12 inch TISSUE weight gain (g) (1000mL void - 1 minute wait - 10 min under load) | | | Backsheet Average Hydrostatic Pressure (cms) | Backsheet Stdev Hydrostatic Pressure (cms) | Backsheet Minimum Hydrostatic Pressure (cms) | Underpad Air Permeability (cfm) | Backsheet Air Permeability (cfm) | ASTM E96-95 MVTR 37 deg C / 50% RH (g/sq.m/day) |
|---|---|---|---|---|---|---|---|---|---|---|---|---|---|---|
| | | | | Leak test visual (Pass / Fail) (1000mL void - 1 minute wait - 10 min load) | | Average | Stdev | Max | | | | | | |
| A | 36x36 Premium Underpad Control | | | 3/0 | Light condensation | 0.076 | 0.018 | 0.096 | 211.2 | 15.7 | 199.0 | 0.12 | 0.12 | 1867 |
| B | As A only 47gsm SMMMMS FC Treated Backsheet | 2 | 142.6 | 3/0 | Heavy condensation | 0.409 | 0.083 | 0.465 | 85.1 | 5.7 | 76.8 | 18.40 | 28.56 | 2195 |
| C | As A only 60gsm SMMMS Untreated Backsheet | | | 3/0 | Heavy condensation | 0.335 | 0.184 | 0.444 | 83.3 | 5.3 | 75.7 | 16.42 | 30.64 | 2292 |
| D | As A only 70gsm SMMMS Untreated Backsheet | | | 3/0 | Heavy condensation | 0.396 | 0.052 | 0.452 | 87.7 | 15.3 | 65.7 | 18.82 | 24.86 | 2289 |

| Sample ID | Product Description | Strike Through | Testing Pressure in | Strike Through | Comment | TISSUE weight gain (g) (1000mL void - 1 minute wait - 10 min under load) | | |
|---|---|---|---|---|---|---|---|---|
| | | | | Leak test visual (Pass / Fail) (1000mL void - 1 minute wait - 10 min load) | | Average | Stdev | Max |
| A | 36x36 Premium Underpad Control | 1 | 70.3 | 3/0 | Light condensation | 0.083 | 0.030 | 0.105 |
| B | As A only 47gsm SMMMMS FC Treated Backsheet | | | 3/0 | Heavy condensation | 0.445 | 0.168 | 0.627 |
| C | As A only 60gsm SMMMS Untreated Backsheet | | | 3/0 | Heavy condensation | 0.419 | 0.175 | 0.596 |
| D | As A only 70gsm SMMMS Untreated Backsheet | | | 3/0 | Heavy condensation | 0.361 | 0.155 | 0.468 |

FIG. 2A

Dead Weight Hard Surface Underpad Strike Through Testing

| Example/Control | Description of Underpad | Core Type | Backsheet | Total Tested | Pass | Fail | Number passed with very small spots of strike through | Total Average Signal Pad Weight Gain from Condensation and Strike Through | Average Signal Pad Weight Gain from samples with no strike through Condensation Only (g) | Average Signal Pad Weight Gain for Underpads with visible Strike Through (g) | Average amount of Liquid Strike through (condensation subtracted) for the samples with Visible Strike Through (g) | Strike through observations | Average Backsheet Hydrostatic Pressure (cm) | Backsheet air permeability (cfm) | Underpad air permeability (cfm) |
|---|---|---|---|---|---|---|---|---|---|---|---|---|---|---|---|
| Control 38 | A inlaid core with Microporous backsheet | SAP/Fluff | Mit Film Bilaminate control | 8 | 8 | 0 | 0 | 1.03 | 1.03 | NA | NA | | 211.2 | 0.11 | 0.12 |
| 65 | Airlaid core with 47 gsm SMMMMS with ABxAS treatment | SAP/Fluff | 47gsm SMMMMS with ABxAS treatment | 5 | 5 | 0 | 4 | 3.59 | 3.63 | 3.57 | -0.06 | | 85.1 | 28.6 | 28.4 |
| 67 | Airlaid core with 70 gsm SMMMS backsheet | SAP/Fluff | 70gsm SMMMS | 13 | 12 | 1 | 7 | 2.98 | 2.84 | 3.06 | 0.35 | The size failure load is provide in the nonwoven | 87.7 | 24.9 | 28.4 |
| 68 | Covidien S&S Wings Breathable Underpad | Fluff only | 27 gsm S&S | 1 | 0 | 1 | NA | 196.70 | NA | 196.70 | NA | Significant strikethrough | 5.3 | 134.0 | |
| 71 | S&S Fluff Core over 70 gsm SMMMMS | Fluff only | 70gsm SMMMS | 3 | 0 | 3 | NA | 4.62 | NA | 4.62 | NA | | 85.1 | 28.6 | |
| 73 | Airlaid core with 2 layers of 47gsm SMMMMS ABxAS | SAP/Fluff | 2 layers of 47 gsm SMMMMS AB Treated | 3 | 3 | 0 | 0 | 2.88 | 2.88 | NA | NA | | 120.3 | 35.2 | |
| 75 | Airlaid core over 27gsm untreated Meltblown R&S + 47gsm SMMMMS AS treated | SAP/Fluff | 27gsm Meltblown only R&S + 47gsm SMMMMS AS treated | 1 | 1 | 0 | 0 | 2.73 | NA | 2.73 | less than 1 drop (1 full drop=0.6 g) | | 90.3 | 28.1 | |
| 77 | Covidien SM8288 Wings Quilted Breathable Underpad | SAP/Fluff | 27 gsm S&S | 1 | 0 | 1 | NA | 76.40 | NA | 76.40 | NA | Significant strikethrough | 5.3 | 134.0 | |

FIG. 2B

Multiple Insult Bed Strikethrough Testing

| Example/Control | Core Type | Backsheet | Number of backsheet layers | Alcohol repellent (AR) treatment | AS treatment | First 250ml insult signal pad weight gain from condensation and strike through (g) | Second 250ml insult signal pad weight gain from condensation and strike through (g) | Average signal pad weight gain from samples with no strike through condensation only (g) | Average signal pad weight gain for underpads with visible strike through (g) | Strike through observations | Average backsheet hydrostatic pressure (cm) | Backsheet air permeability (cfm) | Underpad air permeability (cfm) |
|---|---|---|---|---|---|---|---|---|---|---|---|---|---|
| 94 | Fluff & SAP | Microporous Film Bilaminate control | 2 | | | 1.03 | 5.32 | 5.32 | NA | | 211.2 | 0.12 | 0.12 |
| 82,87,93 | Fluff & SAP | 60gsm SMMMMS no treatment | 1 | | | 2.28 | 60.50 | NA | | through, 1st insult no strike through | 113 | 19.4 | 14.3 |
| 107, 113, 118 | Fluff & SAP | 60gsm SMMMMS FC Treatment | 1 | X | | 2.18 | 5.04 | 4.73 | 5.19 | Very light spotting, all on the 2nd insult | 118.7 | 17.3 | |
| 80, 83, 85 | Fluff & SAP | 70gsm SMMMMS no treatment | 1 | X | | 1.74 | 36.40 | NA | | through, 1st insult no strike through | 128 | 15.1 | 11.8 |
| 108, 111, 116 | Fluff & SAP | 70gsm SMMMMS FC Treatment | 1 | X | | 1.97 | 4.57 | 3.66 | 5.03 | Very light spotting, all on the 2nd insult | 130.7 | 14.1 | |
| 109, 112, 119 | Fluff & SAP | 70gsm SMMMMS FC+AS Treatment | 1 | X | X | 2.01 | 4.85 | 3.60 | 5.48 | Very light spotting, all on the 2nd insult | 116.5 | 16.2 | |
| 88 | Fluff & SAP | 47gsm SMMMMS with FC+AS treatment | 1 | X | X | 2.24 | 6.67 | NA | NA | Lots of light spotting on 2nd insult | 85.1 | 28.60 | 18.40 |
| 92 | Fluff & SAP | 50gsm SMMMMS no treatment | 1 | | | 3.17 | NA | NA | NA | 1st insult, did not test 2nd insult | 102 | 27.00 | 17.90 |
| 100 | Fluff & SAP | 2 Layers of 50gsm SMMMMS no treatment | 2 | | | 2.39 | 8.94 | NA | NA | Strike through on 2nd insult | | | |
| 101 | Fluff & SAP | 2 Layers of 47gsm SMMMMS FC+AS Treatment | 2 | X | X | 2.13 | 4.46 | 4.46 | NA | No strike through | 120.3 | 15.20 | |
| 110 | Fluff & SAP | 2 Layers of PFN 34 gsm FC+AS Treated | 2 | X | X | 1.84 | 3.59 | NA | 3.59 | One 5/8ths inch diameter spot | 77.2 | 30.4 | |
| 121 | Fluff & SAP | SMMMS 34 gsm AS against core + SMMMS 34 gsm FC+AS back | 2 | X | X | 2.44 | 9.20 | NA | 9.20 | over 20 spots, some as large as 2 inches in diameter | | | |
| 115 | Fluff & SAP | SMMMMS 34 gsm FC+AS treated against core, 47 gsm SMMMMS FC&AS Treatment back | 2 | X | X | 2.11 | 2.95 | 2.95 | NA | No strike through | | | |
| 114 | Fluff & SAP | 34 gsm SMMMMS FC+AS against core + 44 gsm SMMMMS FC+AS back | 2 | X | X | 2.32 | 5.10 | 5.10 | NA | No strike through | | | |
| 105 | Fluff & SAP | 34 gsm FC+AS against core+ 44 gsm FC+AS outer layer | 2 | X | X | 2.28 | 5.93 | 5.93 | NA | No strike through | | | |
| 106 | Fluff & SAP | 22 gsm SMMMMS AS Treatment against the core + 47 gsm SMMMMS FC+AS outer layer | 2 | X | X | 2.49 | 6.07 | NA | 6.07 | one 1/4 inch and one 1/8th inch spot | 84 | 21.80 | |
| 117 | Fluff & SAP | 47 gsm SMMMMS FC+AS against core + 34 gsm SMMMMS FC+AS outer layer | 2 | X | X | 2.32 | 5.10 | 5.10 | NA | No strike through | | | |
| 122 | Fluff & SAP | 34 gsm SMMMMS FC+AS against core + 44 gsm SMMMMMS FC+AS outer layer | 2 | X | X | 2.14 | 5.06 | 5.06 | NA | No strike through | | | |

FIG. 2C

BREATHABLE ABSORBENT ARTICLE

The present application for patent claims priority to U.S. Provisional Application No. 62/903,477, titled "Breathable Absorbent Article," filed Sep. 20, 2019, the disclosure of which is incorporated herein by reference in the entirety.

FIELD OF THE INVENTION

The present disclosure relates generally to an absorbent article. Specifically for an article that exhibits water resistance while still remaining breathable that is usable with a low-airloss-bed.

BACKGROUND

Current Absorbent articles may be configured to collect and/or absorb body fluid discharge, such as urine, or other aqueous body fluids. Examples of absorbent articles include disposable diapers or diaper inserts, adult incontinent pads or briefs, feminine hygiene products, training pants, and other articles that may be disposed against a body surface, by infants or adults. One example of an absorbent article is an underpad, which may be suitable for use with patient bedding to help protect a mattress from fluids.

SUMMARY

This summary is provided to introduce a selection of concepts in a simplified form that are further described below in the DETAILED DESCRIPTION. This summary is not intended to identify key features of the claimed subject matter, nor is it intended to be used as an aid in determining the scope of the claimed subject matter.

In accordance with one aspect of the disclosure, an absorbent article with significantly improved breathability is disclosed. The absorbent article may for example be useable to cover at least a portion of a low-air-loss bed for patient care in the medical field. For example, the absorbent article may be an air-permeable underpad configured to prevent liquid from passing from a first side of the absorbent underpad to a second side of the absorbent underpad. The underpad may further include a topsheet layer, and an absorbent core. The absorbent core may for example comprise any one or a combination of absorbent fibers or a superabsorbent polymer. In addition, the absorbent underpad may include a non-woven substrate backsheet including at least a first layer of spunbond fibers, a second layer of spunbond fibers and a first layer of meltblown fiber and a second layer of meltblown fibers. In one example the underpad may be configured to cover at least a portion of a surface or low-air-loss bed with the second side of the absorbent article facing an upper surface of the low-air-loss bed or other surface. The backsheet may be configured to prevent liquid absorbed by the absorbent core of the underpad from passing to the second side of the absorbent article and to the surface below. The hydrostatic pressure of the backsheet may be greater than or equal to 60 centimeters based on the American Association of Textile Chemists and Colorists (AATCC) Test Method 127-2008. In one example, the hydrostatic pressure may be less than or equal to 190 centimeters based on the same test method. In another example, the hydrostatic pressure of the absorbent article may be between 60 and 170 centimeters and more preferably ranges from 80 to 140 centimeters. In another example, the absorbent underpad backsheet may have a hydrostatic pressure that ranges from 75 centimeters to 170 centimeters. In yet another example, the absorbent underpad backsheet may have a hydrostatic pressure that ranges from 105 centimeters to 190 centimeters. In addition, the air permeability of the underpad may be greater than 5 cubic feet per minute based on the American Society for Testing and Materials (ASTM D737-18) Standard Test Method for Air Permeability of Textile Fabrics. In another example, the air permeability of the underpad may range from 5 to 35 cubic feet per minute and more preferably ranges from 10 to 34 cubic feet per minute. At least one or a combination of the non-woven substrate, the topsheet and/or the absorbent core may be treated with an alcohol repellent ("AR") treatment or liquid repellent treatment. In one example, the nonwoven backsheet may be Fluorocarbon or Silicone treated resulting an AR rating of between about 6 and 8 according to Nonwovens Standard Procedures ("NWSP") NWSP 080.8.RO published by EDANA and INDA. More preferably, the backsheet may have an AR rating of between 7 and 8 according to NWSP 080.8.RO.

In another aspect of the disclosure, a system is disclosed for providing an absorbent, air-permeable liquid barrier between a patient and a low-airloss-bed, the system may include a topsheet layer, an absorbent core comprising fibers or a superabsorbent polymer; and a non-woven substrate backsheet. The non-woven backsheet may include a first layer of spunbond fibers, a second layer of spunbond fibers, and a first layer of meltblown fibers and/or a second layer of meltblown fibers, wherein the topsheet layer, the absorbent, core, and the non-woven substrate are configured to cover at least a portion of the low-airloss-bed and the backsheet is configured to provide a liquid resistant barrier between the absorbent core and the low-airloss-bed. The hydrostatic pressure of the backsheet may be greater than or equal to 60 centimeters based on the American Association of Textile Chemists and Colorists (AATCC) Test Method 127-2008. The air permeability of the backsheet may be greater than 5 cubic feet per minute based on the American Society for Testing and Materials (ASTM D737-18) Standard Test Method for Air Permeability of Textile Fabrics. In another example, the air permeability of the backsheet may range from 5 to 35 cubic feet per minute and more preferably ranges from 10 to 34 cubic feet per minute. At least one or a combination of the non-woven substrate, the topsheet and/or the absorbent core may be treated with an alcohol repellent ("AR") treatment or liquid repellent treatment. In one example, the nonwoven backsheet may be Fluorocarbon or Silicone treated resulting an AR rating of between about 6 and 8 according to Nonwovens Standard Procedures ("NWSP") NWSP 080.8.RO published by EDANA and INDA. More preferably, the backsheet may have an AR rating of between 7 and 8 according to NWSP 080.8.RO.

Additional advantages and novel features of these aspects will be set forth in part in the description that follows, and in part will become more apparent to those skilled in the art upon examination of the following or upon learning by practice of the disclosure.

BRIEF DESCRIPTION OF THE DRAWINGS

The novel features believed to be characteristic of aspects of the disclosure are set forth in the appended claims. In the description that follows, like parts are marked throughout the specification and drawings with the same numerals, respectively. The drawing figures are not necessarily drawn to scale and certain figures may be shown in exaggerated or generalized form in the interest of clarity and conciseness. The disclosure itself, however, as well as a preferred mode of use, further objects and advantages thereof, will be best understood by reference to the following detailed description of illustrative aspects of the disclosure when read in conjunction with the accompanying drawings, wherein:

FIG. 2A is a chart showing testing results of various examples in accordance with one aspect of the disclosure;

FIG. 2B is a chart showing testing results of various examples in accordance with one aspect of the disclosure;

FIG. 2C is a chart showing testing results of various examples in accordance with one aspect of the disclosure;

DETAILED DESCRIPTION

Figure 1:
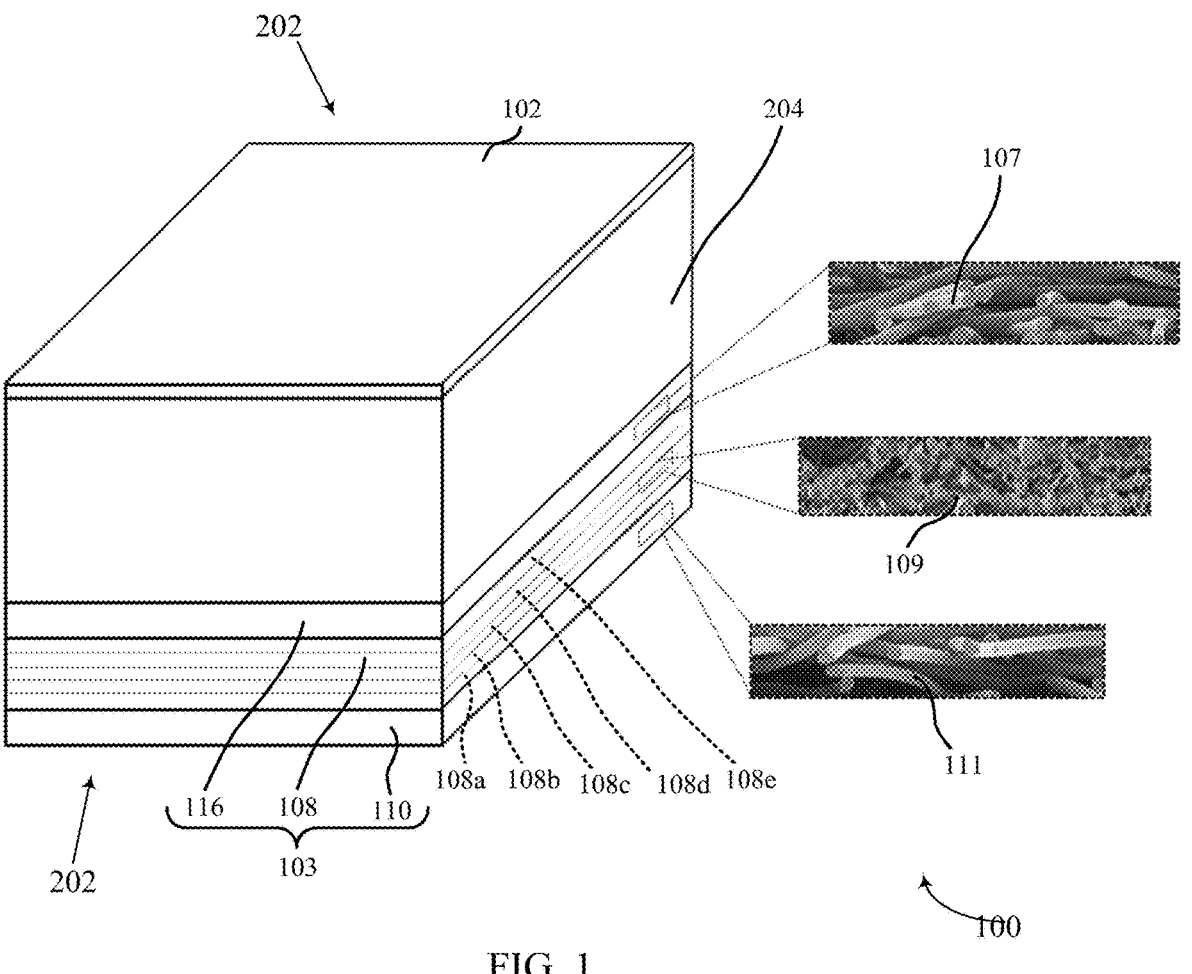
FIG. 1 is a partial cross-section view of one example absorbent article in accordance with one aspect of the disclosure.
Figure 3A:
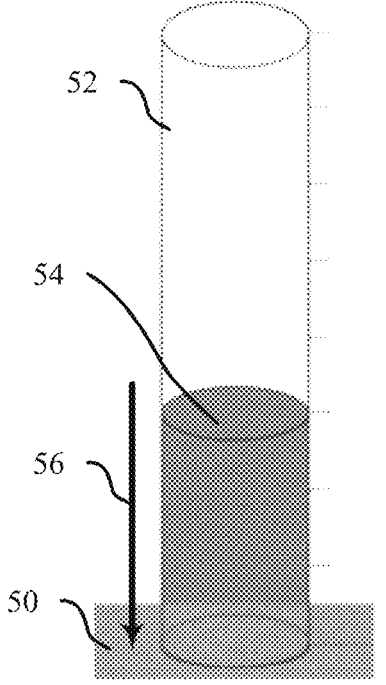
FIG. 3A-3B are diagram views of a related art hydrostatic pressure test.
Figure 3B:
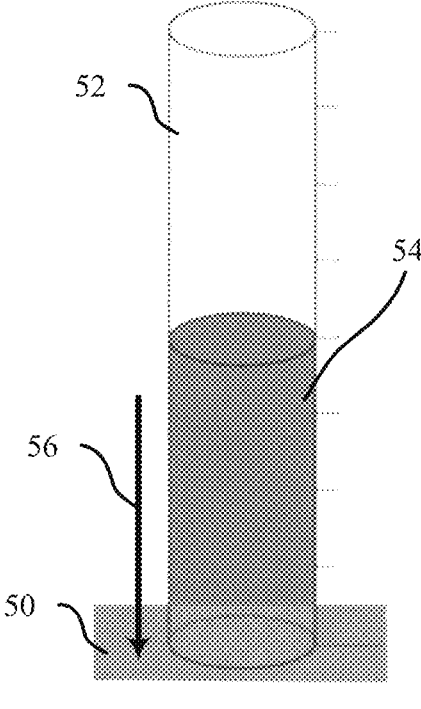

The following includes definitions of selected terms employed herein. The definitions include various examples and/or forms of components that fall within the scope of a term and that may be used for implementation or context. The example definitions are not intended to be limiting.

"article," or "absorbent article" as used in the specification may refer to consumer products whose primary function is to absorb and/or retain and/or prevent leakage of soils, wastes, and/or other fluids. "Article" or "absorbent article" may also refer to an absorbent article generally worn by infants or incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner). In one example, "article" or "absorbent article" may refer to a sheet or drape that is dimensioned or otherwise configured to cover at least a portion of or an entire bed, chair or other seating surface, operating table or procedure table and absorb and/or prevent leakage of soils wastes, and/or other fluids. In one example, an absorbent article may be an underpad for covering at least a portion of a low-airloss-bed.

Throughout the disclosure, the term "substantially," "approximately" or "about" may be used as a modifier for a geometric relationship between elements or as a modifier for a numeric value. While the terms substantially, approximately, and about are not limited to a specific variation and may cover any variation that is understood by one of ordinary skill in the art to be an acceptable variation, some examples are provided as follows. In one example, the terms substantially, approximately, or about may include a variation of less than 10% of the dimension of the object or component or numerical value. In another example, the terms substantially or approximately may include a variation of less than 5% of the object or component or numerical value. In another example, the terms substantially or approximately may include a variation of less than 3% of the object or component or numerical value or less than 2% of the object or component or numerical value. If the terms substantially, approximately, or about are used to define the angular relationship of one element to another element, one non-limiting example of the terms may include a variation of 5 degrees or less. These examples are not intended to be limiting and may be increased or decreased based on the understanding of acceptable limits to one of ordinary skill in the art.

The term "nonwoven" as used in the specification may refer to a material made from continuous (long) filaments (fibers) and/or discontinuous (short) filaments (fibers) by processes such as spunbonding, meltblowing, wetlaying, carding, airlaid and the like. Nonwovens do not have a woven or knitted filament pattern. It is to be appreciated that nonwovens having various basis weights can be used in accordance with the methods herein. For example, some nonwovens may have basis weight of about 7 gsm to about 100 gsm, or more preferably between 15 gsm and 90 gsm. In another aspect nonwovens may have a basis weigh of about 7 gsm to about 120 gsm. All of the aforementioned examples and may include all 1 gsm increments within the above-recited range and all ranges formed therein.

"Substrate" as used in the specification may describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils. These materials may be used alone or may comprise two or more layers laminated or otherwise joined together. As such, a web is a substrate.

"Insult," as used in the specification, may refer to liquid or soil that may be desired to be absorbed and/or isolated by an article. The term "insult side" may refer to a side of an article that is designed to come into contact with and/or absorb insult. The term "non-insult side" may refer to a side of an article opposite the insult side. The non-insult side may contact a surface that is to be protected or otherwise isolated from insult that the insult side may be exposed to.

"Strikethrough," as used in the specification may refer to liquid that leaks or passes through an article. For example, an article's ability to resist strikethrough may refer to properties of the article that prevent liquid or insult from passing from a first side of the absorbent article underpad to a second side of the absorbent article. One non-limiting indicator of an articles ability to resist strikethrough is a measure of hydrostatic pressure of the backsheet in centimeters based on the American Association of Textile Chemists and Colorists (AATCC) Test Method 127-2008, one example of which is described in further detail below. Another non-limiting indicator of an articles ability to resist strikethrough are surface or bed testing procedures, one example of which is described in further detail below.

"Air permeability," as used in the specification, may refer to the volume of air (e.g., in cubic feet) that passes through a given area of the material tested (e.g., a square foot) in a given time period (e.g., a minute) under predetermined testing conditions. While various ways of measuring air permeability of an article are known and may be used, one suitable method of measuring air permeability involves the use of a suitable testing machine and the testing protocol set forth under American Society for Testing and Materials (ASTM) D737-96.

"Hydrostatic pressure," as used in the specification, may refer to a force distributed over an area of an article by water or hydrostatic head, which may be used to determine the water penetration resistance or water resistance or a characteristic of a fabric or article to resist wetting and penetration by articles. While various ways of measuring the air permeability of an article are known and may be used, one suitable method of measuring hydrostatic pressure involves the use of a suitable testing machine and the testing protocol set forth under American Association of Textile Chemists and Colorists ("AATCC") Test Method 127-2008.

The current disclosure relates to an absorbent and breathable article that may for example be used as an underpad. While throughout the disclosure an underpad is the primarily example described, it is noted that the disclosure is applicable to any article that is used to absorb and/or retain and/or prevent leakage of soils, wastes, and/or other fluids. In addition, the article may be disposable. The article described herein provides water and leak resistance while providing a significant increase in breathability and moisture vapor transmission rate when compared to other similar articles on the market. The increase in breathability offers at least one of the following advantages: a reduction in patient discomfort; the ability to decrease the frequency at which the article needs to be replaced; a decrease in waste; cost savings; and management of a patients skin temperature and/or moisture, to name a few examples. Further, improved management of a patients microclimate due to the increase in breathability of the disclosed article, may provide improvements in patient skin temperature and/or a decrease in moisture and may also provide a decrease in adverse effects to a patient, such as pressure ulcers, for example.

One example scenario in which improved breathability of underpads provides an advantage is use under a patient in a hospital bed and/or low-air-loss beds or surfaces. Low-air-loss beds and surfaces have known advantages preventing and treating skin ulcers. One example of a low-air-loss bed or mattress includes a number of small holes that provide air flow to the patients. Underpads can significantly reduce the effects and/or efficiency of a low-air-loss bed or mattress. Thus, an underpad with improved breathability while still providing liquid absorption and leak resistance may be especially desirable when used in conjunction with a low air-loss-bed. One example of a low-air-loss bed that may be beneficially used with the current disclosure is marketed under trade name Envision® manufactured by Hillrom™ of Batesville Ind. However, the aforementioned example is not intended to be limiting as an underpad or absorbent article in accordance with the current disclosure may be usable with any known low-air-loss bed, mattress, or chair, to name additional examples. The underpad or absorbent article may be particularly useful in the medical field for care of patients.

Since low-air-loss beds may be used to increase patient comfort and reduce injuries (e.g., pressure ulcers) and skin breakdown, especially when a patient is required to remain in a bed for extended periods of time, microclimate management becomes an important consideration in ensuring a patient's health. Underpads, other absorbent articles, and linens may be placed on top of low-air-loss beds to manage incontinence, drainage and/or to improve patient comfort. However, coverings on air-loss-beds may decrease the performance of the low-air-loss bed and/or negatively affect microclimate. One publication that discusses these effects is titled "Linen Usage Impact on Pressure and Microclimate Management," by Rachel Williamson et al., published by Hill-Rom® on Jan. 21, 2009, the entire contents of which is incorporated by reference herein. Articles in accordance with the current disclosure may provide improved microclimate and low-air-loss bed performance, while providing an effective barrier and management of incontinence, drainage and/or improvement of patient comfort.

As described in further detail below, an underpad may include an absorbent core or layer and a backsheet or second layer that provides a liquid resistant barrier. One type of backsheet that provides leak resistance is a microporous backsheet. Microporous backsheets may include either a polymeric or microporous film to provide a barrier for water or moisture while still allowing for some airflow and the passage of water vapor. In general, a microporous film may contain billions of micropores, many of which may be connected. In most cases the pore sizes are smaller than a drop of water, so water droplets cannot penetrate unless a significant amount of pressure is applied. However, the pores may be larger than water vapor molecules, so steam and perspiration can penetrate the film. Microporous film backsheets are typically laminated to a nonwoven to strengthen the underpad, with the microporous film against the core and a nonwoven layer laminated to the film. In addition, an underpad is often used to re-position patients on a bed, and backsheet has to be resistant against tearing.

However, one significant disadvantage of microporous films as backsheets, especially in the setting of incontinence articles or other articles is that the air permeability or ability for air to flow through the film is low. Thus, polymeric or microporous films still cause a buildup of moisture and/or increase in temperature at a patients skin. Further, the restriction of airflow through polymeric or microporous films also significantly decreases the performance of low-air-loss beds.

A cross section of one example of an article or underpad of the current disclosure is shown in FIG. 1 with partial magnified views of each layer of a nonwoven backsheet 103. The nonwoven backsheet 103 may provide breathability while still preventing liquid from passing from the insult side 202, which may be interchangeably referred to as a first side of the article to the non-insult side 202, which may be interchangeably referred to as a second side of the article. The backsheet 103 may include a first spunbond layer 110 comprised of first spunbond fibers 111, a meltblown layer 108 comprised of meltblown fibers 109, and a second spunbond layer 116 comprised of second spunbond fibers 107. It is noted that while FIG. 1 shows a number of meltblown layers 108a-108e and a first and second spunbond layer 110 and 116, any number or combination of the aforementioned layers may be provided. For example, the backsheet 103 may include an additional or two additional meltblown layers and/or may have the second spunbond layer 116 removed. In addition, the backsheet 103 may include two additional spunbond layers and a second meltblown layer therebetween. In yet another example, the article or underpad may include two or more backsheets (e.g., backsheet 103) comprising the aforementioned layers and features.

Each of the spunbond (e.g., 106 and 110) and/or meltblown layers (e.g., 108) may be formed from a series of fibers, bonded together by chemical, mechanical, heat, and/or solvent treatment. Further, the fibers of each of the spunbond and/or meltblown layers may be formed of any one of or a combination of polypropylene, polyethylene, polyester, polyimides, or any thermoplastic polymer, including biodegradable polymers, to name a few examples.

In one example, the aforementioned spunbond layers (e.g., 116 and/or 110) may be composed of longer interlocked continuous filaments than the filaments forming the meltblown layer 108. The process of forming the spunbond layer may comprise steps of: filament extrusion; filament orientation; filament laydown; and web bonding. The spunbond process may for filaments from chips of any one of or combination of the aforementioned materials as the "material to be extruded." The material to be extruded may then be provided to an extruder. Once the pellets are extruded a spin pump or spin pumps may form spinnerets from the extruded pellets. Cooling or operating air may then be provided to the spinnerets to at least partially solidify the extruded pellet material. The at least partially solidified spinnerets may then be supplied to a draw-off or laydown system, which provides the solidified fibers to a web forming belt. The web formed on the belt may then be provided to a bonder that bonds the filaments together. Methods of binding the individual fibers may include any one or a combination of applying binders; applying solvents; applying heat and/or pressure to melt or partially melt the individual fibers to one another and or providing a heated needle loom met individual fibers to one another. It is noted that while various processes and process variations have been given here as an example. The disclosed under pad does not necessarily need to be formed using the aforementioned processes and may be formed using any known method in the art.

The meltblown layer 108 may be a liquid barrier layer. In one example, the meltblown layer 108 may be produced by providing short melted polymer fibers through a spin net and/or by providing the material through passages or multiple passages. The passages or die may be arranged so that the material, which may generally have a lower viscosity than the material provided during the spundbond layer is provided through the die and intersects with passages that provide heated and/or pressurized air and/or gas to the extruded fibers. The forces imparted on the material cause short fibers to be formed that are self-adhering and are provided to a collection screen, rotating collector, and/or meltblown web. The individual fibers may be fully or partially solidified on the collection screen, winder and/or web. Some other methods of forming the liquid barrier layer may include may include electrospinning, for example. The fibers 109 of the meltblown layer 108 may be extremely fine fibers and significantly smaller in cross-section than the spundbond fibers 107 and or 111 of layers 110 and 116 discussed in further detail below. In one example, the meltblown fibers 109 of the meltblown layer 108 may range between 0.05 and 10 micrometers. In another example, the individual fibers 109 of the meltblown layer may range between 0.05 and 10 micrometers with an average fiber diameter of 1 to 2 micrometers. In yet another example, the individual fibers 109 of the meltblown layer may range between 0.05 and 5 micrometers with an average fiber diameter of 1 to 2 micrometers. The small diameter of individual fibers 109 of the meltblown layer provide a barrier to prevent water or other liquids from passing through the meltblown layer 108. However, since the meltblown fibers 109 have a very small average fiber diameter they may have low intrinsic strength. Thus, spunbond layers 110 and 116 may be added to the meltblown layer 108 to provide strength to the backsheet 103. Further, as shown in FIG. 1, the meltblown layer 108 may comprise a number of meltblown "layers" formed based on the number of beams of meltblown provided during the manufacturing process. It is noted that each of "layers" 108a, 108b, 108c, 108d, and 108e, may actually not be layers with boundaries therebetween but may be comprised of fibers that are intertwined between and connecting each "layer" during the manufacturing process. For example, each of the aforementioned layers 108a, 108b, and/or 108c may be formed on a single line with multiple beams providing the extrusions for forming each layer. For example, a single line may or web former may include a spunbond extruder, a meltblown extruder, and a spunbond extruder to form a nonwoven which may be abbreviated as an "SMS nonwoven." Likewise, a single web forming apparatus or line may include a first spunbond extruder a first meltblown extruder, a second meltblown extruder, a third meltblown extruder, a fourth meltblown extruder, and a second spunbond extruder to form a nonwoven which may be abbreviated as an "SMMMMS nonwoven." Thus, as shown in FIG. 1, one example of the article 100 may include a single meltblown layer 108 or beam and up to five meltblown layers "SMMMMMS" or beams 108a-108e. In one example, the additional meltblown layers may provide an additional barrier and water resistance to the article. In one example, it may be preferable for the non-woven backsheet 103 to include three "SMMMS" to five "SMMMMMS" meltblown beams or layers. In another example, it may be preferable for the nonwoven backsheet 103 to include four "SMMMMS" or five "SMMMMMS" meltblown beams or layers.

The first and second spunbond layers 110 and 116 be produced using known methods. In one example, the spunbond fibers 111 and 107 of the first and second spunbond layers 110 and 106 may be formed by depositing extruded, spun filaments on to a collecting belt in a uniform random manner by bonding the individual fibers (e.g., 111 and 108). The fibers are separated during the laying process by air jets and/or electrostatic charges. The filaments are bonded by either melting caused by heated air from the air jets and/or by applying heating rolls or hot needles. The average cross sectional diameter of the spundbond fibers (e.g., 107 and 111) may range between 11-50 micrometers with an average fiber diameter of 15-19 micrometers. In another example, the individual fibers of the spunbond layer may average between from 16-18 micrometers or from 13-18 micrometers. As mentioned above, it is noted that while the first and second spunbond layers 110 and 116 and the meltblown layer(s) 108 are referred to as layers, they may not actually comprise boundaries therebetween and may be intertwined with one another during the manufacturing process when formed inline.

The article 100 may further include an absorbent layer or core 204. The core 204 may be comprised of fluff pulp, which may hereinafter be interchangeably referred to as fibers, and may additionally include super absorbent polymer (SAP). The fluff pulp be formed of any know material including long or short fiber softwoods, cellulose acetate fibers, rayon fibers, lyocell fibers, polyacrylonitrile fibers, cotton fibers or cotton linter fibers. The fluff pulp in the core 204 may provide bulk and/or absorbency to the article. The SAP may include any known water-absorbing polymer. While the disclosed core is not limited to including SAP, providing a core with SAP may be advantageous for locking in moisture. One advantage of SAP is that if an incontinence article is insulted, any moisture is kept away from a patient or users skin. Some examples of a SAP usable with the current disclosure may include any one of or a combination of a natural or synthetic polymer with a chemically bonded hydrophilic groups or polymer selected from the group comprising a sodium neutralized cross-linked polyacrylate or polysaccharides; polymerized acrylic acid blended with sodium hydroxide (sodium polyacrylate); polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile, to name a few examples. The core 204 may provide absorption and retention of any liquids or fluid on the insult side 202 of the article.

In one example, the core may be formed on an airlaid line wherein a web of fibers and SAP are laid on a pre-formed tissue or layer. The core may be bonded using high pressure using an embossed roll through a high pressure nip. The absorbent core may also be bonded by spraying an adhesive or other material such as latex onto the material and/or via the addition of synthetic air bonding fibers and bonded with high pressure and/or temperature. Another bonding method is through-air bonding where warmed air is used to heat up the formed web. In the aforementioned process, the synthetic air bonding fibers have a lower melting temperature than the burning temperature of fluff pulp or melting temperature of any synthetic fiber use. Thus, the article may be heated causing the synthetic or sheath polymer to melt or partially melt casing the bonding of the structure. The bonding fiber may include any one of a polypropylene or polyester which may be surrounded by a polymer having a low melting ting temperature. In one example, the core may contain approximately 5% synthetic bonding fibers. Combinations of these aforementioned absorbent core bonding methods may be used together.

In addition to the aforementioned layers, a top layer 102 may be provided to bind or otherwise provide an outer surface to the aforementioned layers. The top layer 102 may for example be comprised of a porous material, such as a spunbond nonwoven. Further, It is noted that the order of layers shown in FIG. 1 are shown as an example. Thus, the disclosure is not limited to the aforementioned layers or order of layers. Further, additional layers may be provided to the article 100 without departing from the scope of the disclosure.

In addition to the aforementioned features any one of or a combination of the layers of article 100 may be liquid repellent or alcohol resistance ("AR") treated. While throughout the disclosure AR treatment may be referred to, the term AR treatment may refer to any liquid or water repellent treatment. In one example, the backsheet is AR coated to prevent wetting or contact of water or liquid that may be received on the insult side 202 of the article with the meltblown layer 108. As shown in the test results described in further detail with respect to FIG. 4 below, AR treatment of the backsheet 103 improves liquid resistance of the article significantly; especially during the bed testing protocol discussed in further detail below. The AR treatment may include any known method of AR or water repellency treatment. Some examples include and are not limited to treatment with fluorocarbons; polydimethylsiloxane; treatment with compounds formed by reacting stearic acid and formaldehyde with melamine. Other AR or liquid repellent treatments may include and are not limited to: Unidyne TG-5502™, and/or Unidyne TG 5601™, and/or Undyne XF™, Series non-fluorinated repellent finish all manufactured by Daikin Chemicals; Teflon™ treatments which may include Phobol® CP/ND, Phobotex, Phobol® Extender SFB, Zelan™ and/or Capstone™ based treatments, all manufactured by Huntsman or treatment with known fluorocarbon alternatives such as OrganoTex®, manufactured by Organotex at Linjalvagen 9: SE-187 66 Taby Sweden; Siltech® E-2178 Cross-linked Alkyl Siloxane Emulsion and/or Siltech® E-2152 Cross-linked Amino Siloxane Emulsion manufactured by Siltech. In another example, the AR or liquid repellency treatment may be provided as a melt additive during and/or before forming of the non-woven. Some examples may include polymer additives such as HYDREPEL®, manufactured by Goulston Surface Modification Technologies. In one example, at least one or a combination of the non-woven substrate, the topsheet and/or the absorbent core may be treated with an alcohol repellent ("AR)" treatment or liquid repellent treatment. In one example, the nonwoven backsheet may be Fluorocarbon or Silicone treated resulting an AR rating of between about 6 and 8 according to Nonwovens Standard Procedures ("NWSP") NWSP 080.8.RO published by EDANA and INDA. More preferably, the backsheet may have an AR rating of between about 7 and 8 according to NWSP 080.8.RO. One example of the aforementioned testing procedure is described in further detail below. In some examples, any single layer (e.g., a single meltblown or spunbond layer) of the backsheet may be AR or liquid repellant coated. In examples mentioned below including a plurality of spunbond and/or meltblown layers, any one or a combination of layers may be AR or liquid repellant coated. In yet another example, a layer that is not immediately adjacent to the absorbent core, may be AR or liquid repellant coated. In one example, any one or a combination of layers of the backsheet that are not immediately adjacent to the absorbent core may be AR or liquid repellant coated.

In one example, an air-permeable absorbent underpad is disclosed with a single non-woven backsheet (e.g., backsheet 103 in FIG. 1). The single nonwoven backsheet may comprise one or more spunbond layers and greater than one and preferably greater than two meltblown layers. In examples in accordance with the current disclosure, the nonwoven backsheet may prevent liquid absorbed by the absorbent core of the underpad from passing to the second side of the absorbent article and the hydrostatic pressure of the backsheet may be greater than or equal to 80 centimeters based on the American Association of Textile Chemists and Colorists (AATCC) Test Method 127-2008 (described in further detail below). In another example, the hydrostatic pressure of the backsheet described above may be greater than or equal to 80 centimeters and less than or equal to 190 centimeters using the aforementioned test method. In another example, the hydrostatic pressure of the backsheet described above may be greater than or equal to 100 centimeters. In another example, the hydrostatic pressure of the backsheet described above may be greater than or equal to 100 centimeters and less than or equal to 190 centimeters using the aforementioned test method. In another example, the hydrostatic pressure of the backsheet described above may be greater than or equal to 105 centimeters and less than or equal to 190 centimeters. In another example, the hydrostatic pressure of the backsheet described above may be greater than or equal to 120 centimeters. In yet another example, the hydrostatic pressure of the backsheet described above may be greater than or equal to 120 centimeters and less than or equal to 190 centimeters. The aforementioned examples provide improved breathability of the article while still providing adequate resistance to strikethrough.

In one example, an air-permeable absorbent underpad is disclosed with a multiple non-woven backsheets (e.g., backsheet 103 in FIG. 1). Each of the backsheets may comprise one or more spunbond layers and one or more but preferably greater than two meltblown layers. In examples in accordance with the current disclosure, the nonwoven backsheet may prevent liquid absorbed by the absorbent core of the underpad from passing to the second side of the absorbent article and the hydrostatic pressure of the backsheet may be greater than or equal to 70 centimeters based on the American Association of Textile Chemists and Colorists (AATCC) Test Method 127-2008 (described in further detail below). In another example, the hydrostatic pressure of the backsheet described above may be greater than or equal to 70 centimeters and less than or equal to 160 centimeters using the aforementioned test method. In another example, the hydrostatic pressure of the backsheet described above may be greater than or equal to 80 centimeters. In another example, the hydrostatic pressure of the backsheet described above may be greater than or equal to 80 centimeters and less than or equal to 160 centimeters using the aforementioned test method. In another example, the hydrostatic pressure of the backsheet described above may be greater than or equal to 90 centimeters. In yet another example, the hydrostatic pressure of the backsheet described above may be greater than or equal to 90 centimeters and less than or equal to 160 centimeters. The aforementioned examples provide improved breathability of the article while still providing adequate resistance to strikethrough.

FIG. 2A shows test data with several examples in accordance with one aspect of the disclosure. The test data in FIG. 2A is based a countertop or hard surface test as described in further detail below. As shown in FIG. 2A, control 30, or sample A, included a microporous film backsheet passed the countertop strikethrough test at 2 pounds per square inch ("PSI"). Light condensation was noted and the weight gain, in grams, of a tissue placed below the insulted area of the underpad resulted in an average weight gain of 0.076 grams, due largely to condensation of the warmed saline. The average hydrostatic pressure of the backsheet was 211.2 centimeters. The air permeability of the backsheet averaged 0.12 cubic feet per minute. Similarly at 1 PSI, light condensation was noted and the weight gain of the tissue below the underpad and microporous backsheet was 0.083 grams. While no strikethrough was noted, the air permeability of control 30 was significantly lower the examples of the current disclosure. The higher condensation with samples B, C, D compared with sample A is due to a higher moisture vapor transmission rate ("MVTR") in the nonwoven backsheet underpad samples. The backsheet moisture vapor transmission rate of samples B,C and D is significantly higher than the MVTR of the control 30 backsheet MVTR. A higher MVTR is another advantage that of the article in accordance with the current disclosure.

Sample B, in 2A, for example was a 47 gsm SMMMMS backsheet with fluorocarbon treatment. While condensation, and thus weight gain of the tissue increased in both the 1 PSI and 2 PSI tests, no notable strikethrough was observed. The hydrostatic pressure of sample B averaged 85.1 centimeters, and the air permeability averaged 18.4 cubic feet per minute, a notable increase from the microporous film backsheet in control 30 or sample A, for example. Thus, comparing results of Sample B with control 30 shows one of the shortcomings of microporous films—lack of breathability and the significant increase in breathability of the article in the current disclosure. Samples C and D provided similar results, a significant increase in air permeability when compared to the control 30, while still providing adequate strikethrough performance.

FIG. 2B shows test data with several examples in accordance with one aspect of the disclosure. The testing procedure for the example tests shown in FIGS. 2B and 2C are described in further detail below for reference. As shown in FIG. 2B, control 30 shows one example of a microporous film backsheet. The average hydrostatic pressure for control 30 was 211.2 centimeters. In addition the air permeability of control 30 was 0.12 cubic feet per minute. While there was no observed strikethrough, it is noted that the air permeability of the control was significantly lower than the examples of the current disclosure. Thus, control 30 again shows the lack of breathability of microporous films. Trials 69 and 77 show two examples of current underpads with non-woven backsheets on the market. While trials 69 and 77 show a significant increase in air permeability of 134 cubic feet per minute and thus a significant increase in breathability when compared to control 30; trials 69 and 77 exhibited significant strikethrough in testing. Trials 69 and 77 had both had average hydrostatic pressures of 5.3 centimeters. In addition, trials 65, 67, 73, and 75 show that cores with fluff pulp and SAP perform better in strikethrough testing than cores with only fluff pulp. Trial 75 shows a two layer backsheet where one of the nonwoven layers is a 27 gsm meltblown only nonwoven layer and the outer nonwoven layer is an SMMMMMS.

As shown in FIG. 2C and as described in further detail below, underpads in accordance with the current disclosure provide acceptable strikethrough performance while providing a significant increase in air permeability and thus breathability than underpads that include microporous film. FIG. 2Cs shows test data with several examples in accordance with one aspect of the disclosure. As mentioned above, each of the relevant tests are described in further detail below for reference. As shown in FIG. 2C, control 94, shows one example of an underpad with a microporous film backsheet. The average hydrostatic pressure for control 94 was 211.2 centimeters. In addition the air permeability of control 94 was 0.12 cubic feet per minute. While no there was no observed strikethrough, it is noted that the air permeability of the control was significantly lower than the examples of the current disclosure.

For example, trial 88, included a 47 gsm nonwoven backsheet with four meltblown beams. In addition, the backsheet of trial 88 was fluorocarbon treated. While some strikethrough was noted in the second bed test, the average hydrostatic pressure was 85.1 centimeters and the air permeability was 18.4 cubic feet per minute, which was significantly higher than the control trial 94. Thus, while strikethrough performance was slightly compromised when compared to the control, the strikethrough performance was still acceptable and a significant increase in air permeability was noted.

Trial 101 included two layers of 47 gsm non-woven backsheet each with four meltblown beams. In addition, the backsheet of trial 101 was fluorocarbon treated. No strikethrough was observed in the bed test. The average hydrostatic pressure was 120.3 centimeters and the air permeability was 15.2 cubic feet per minute, which again was significantly higher than the control trial 94.

Trial 106 included a single layer of 22 gsm nonwoven backsheet with three meltblown beams and a 47 gsm fluorocarbon treated with 4 meltblown beams. Minimal strikethrough was observed. The average hydrostatic pressure was 84 centimeters and the air permeability was 21.8 cubic feet per minute, which again was significantly higher than the control trial 94. Thus, while strikethrough performance was slightly compromised when compared to the control, the strikethrough performance was still acceptable and a significant increase in air permeability was noted.

Examples 101, 110, 121, 115, 114 105 and 106 are double nonwoven backsheets, with fluorocarbon ("FC") treatment on at least one of the nonwoven layers. Examples 101, 105, 114 and 115 had no strikethrough. The dual layer nonwoven air permeability is still quite high (example 101) with superior strike through. Structurally there also may be some advantages to having a dual nonwoven SMS structure over a single nonwoven layer. In some examples, only one of the nonwoven layers were treated with FC, while the second layer was not repellent treated. In this example, placing the non-treated nonwoven against the core and the liquid repellent ("FC") treated nonwoven as the outside layer had better strike through performance than orienting the FC treated layer against the core and placing the non-treated layer on the outside.

Example 117 also includes double nonwoven backsheets with a first SMMMMS backsheet against a core with both fluff pulp and SAP, and an SMMMS outer layer. Both of the non-woven layers are liquid repellent ("FC") treated. Example, 122 includes double nonwoven backsheets with a first SMMMS backsheet against a core with both fluff pulp and SAP, and an SMMMMS outer layer. Both of the non-woven layers were liquid repellent ("FC") treated. Both of samples 117 and 122 passed with no strikethrough. Samples 117 and 122 also provided a significant increase in strength. In addition, it was noted that samples with double nonwoven backsheet, especially samples 117 and 122 were more resistant to strikethrough than samples with a single nonwoven backsheet.

Any one or a combination of the aforementioned examples or described aspects may be implemented as an absorbent article, which may for example include but is not limited to a wearable incontinence article such as a diaper, pad, and/or a sheet or other article intended to be draped over or otherwise connected to a patient or an object (e.g., such as a bed, chair, or low-airloss-bed). In another example, the aforementioned examples may be implemented solely for use as an drape or sheet that is used as an underpad on a bed, chair, or low-air-loss-bed. In another example, the aforementioned examples may be implemented specifically for use in a low-airloss-bed and may not be intended to be used as a wearable article such as diaper or other patient wearable garment.

One example aspect of the disclosure is a method of manufacturing an air-permeable absorbent article, such as an absorbent air-permeable underpad. The method may include steps of connecting a topsheet layer and an absorbent core comprising any one or a combination of fibers or a super-absorbent polymer to a backsheet comprised of a non-woven substrate. The non-woven substrate may include any one or a combination of the backsheets discussed above and may be produced on a single production line. In one example the backsheet may for example include a first layer of spunbond fibers, a second layer of spunbond fibers, a first layer of meltblown fibers and a second layer of meltblown fibers. In one aspect, the first and second layers of meltblown fibers may for example be produced between the first and second layer of spundbond fibers.

In one example, the core or airlaid core (e.g., absorbent layer or core 204) may be formed with a meltblown fiber containing non-woven. In the aforementioned example, the non-woven could be formed as a single or multiple layers of meltblown fibers or other absorbent fibers that are formed either as a separate component from the backsheet or as a single or multiple meltblown layers within the backsheet. In one example, the underpad may be formed with a first layer of spunbond fibers, first layer of meltblown fibers and/or a second layer of meltblown fibers (which may function as the absorbent core) and/or a third layer of meltblown fibers and a second layer of spunbond fibers, to name an additional example. It is noted that in the aforementioned example, any one or a combination of meltblown layers and spunbond layers may function as the absorbent core and/or the back-sheet. Likewise in an absorbent article in accordance with the aforementioned example, any number of additional meltblown or spunbond layers may be formed either on a single non-woven production line or in multiple production lines. For example, the aforementioned example may include additional meltblown layers or spunbond layers in addition to the examples discussed above. Further as mentioned above, the absorbent core and/or the backsheet non-woven substrate may be formed on the same production line and wound up together as a single roll which is later separated or otherwise formed or cut into a single or plurality of absorbent articles or underpads.

In another example implementation of the disclosure, a kit or system is disclosed. The kit or system may for example include at least one absorbent article, such as an underpad in accordance with the examples provided throughout this disclosure. The kit or system may for example include any one or combination of the absorbent articles discussed above as an underpad for covering or at least partially covering and providing an air-permeable barrier between a surface that a patient would otherwise come into contact with. In one example, the absorbent article may be usable with a bed or low-air-loss bed having a patient facing surface. Similar to the implementations discussed throughout the disclosure, the underpad may be configured to prevent liquid from passing form a first side of the absorbent underpad to a second side of the absorbent underpad. The kit or system may include a single or multiple packaged absorbent articles. In one example the absorbent article or series of absorbent articles may be packaged in an openable bag or package. For example, the absorbent article or series of absorbent articles may be packaged in a bag that is sealed or otherwise closed to protect the absorbent article(s) from contamination prior to use. The packaging may for example include a perforated section or strip that allows a user to easily open the packaging. In one example, the packaged absorbent article or articles may be sterilized or sanitized either before and/or after the absorbent article(s) are packaged.

In addition to the absorbent article, the package may either contain or have disposed thereon or affixed thereto an instruction sheet or instructions advising a user of the kit or system to place or affix the underpad onto at least a portion of the bed or low-air-loss bed with the second side of the absorbent article facing the patient facing surface of the bed or low-air-loss bed. It is noted that the instruction sheet or instructions may for example include additional information such as any one or a combination of the dimensions of the underpad or an indication of the dimensions of the underpad, the absorbency of the underpad, the materials of the under-pad, the intended use of the underpad, branding information, and/or a website address or quick response code ("QR") code to additional instructions or information. In one example, instructions advising a user of the kit or system to place or affix the underpad onto at least a portion of the bed or low-air-loss bed with the second side of the absorbent article facing the patient facing surface of the bed or low-air-loss bed may be provided digitally as web-based content for example via any one or a combination of text, pictographic or photographic instructions or diagrams and/or videos outlining the installation procedures and other information which may include but is not limited to the examples provided above. In one example, a website address to the aforementioned content and/or a QR code may be provided on any one or a combination of the packaging of the underpad, an instruction sheet or leaflet provided with the underpad, and/or on a surface of the underpad so that a user may easily access content related to the underpad.

Alcohol Repellency Testing

Alcohol Repellency ("AR") testing may be used to measure the resistance of the non-woven to penetration by aqueous isopropanol solutions. The alcohol repellency rating is the highest test solution (described below), that does not penetrate the non-woven specimen within five (5) minutes. To determine the AR of a non-woven the specimen is placed on a horizontal glass plate. Solutions of isopropanol alcohol in deionized water measuring 0, 20, 30, 40, 50, 60, 70, 80, 90, and 100% by volume may be used in testing. One drop of a number 0% test solution is placed on the specimen in three (3) separate locations and the non-woven specimen is observed after five (5) minutes and is observed for penetration. If no penetration is observed the test is repeated with 20% test solution in three new locations of the sample. This process is repeated for each progressively higher number test solution (e.g., in the order shown above) until penetration is observed. The AR rating of the material is the highest number test solution which does not penetrate the specimen with five (5) minutes. For example a AR rating of 7 would indicate that the 70% solution did not penetrate the sample after five (5) minutes and the 80% solution did penetrate the sample. Examples of the aforementioned test are published by the EDANA and INDA in Nonwovens Standard Procedures ("NWSP") NWSP 080.8.RO.

Hydrostatic Pressure Testing

Hydrostatic pressure (i.e., the force distributed over an area of an article by water) or hydrostatic head may be used to determine the water penetration resistance or water resistance (i.e., the characteristic of an article to resist wetting and penetration by water) of articles. Water penetration resistance of an article may be attributed to a number of factors which may include but is not limited to the water repellency of individual fibers, as well as the overall construction and treatment of the fabric.

In general, hydrostatic head is a measure of the height of a column of water a fabric or article can hold or retain before the water starts to seep through or penetrate though the article. FIGS. 1A-B show a simplified example of one method of measuring hydrostatic head of an article. As shown in FIGS. 1A-B, the hydrostatic head of a fabric or article 50 may be determined by sealing a column of water 54 to the article 50. As the amount of water and/or fluid 54 increases, a pressure applied on the article 50 denoted by arrow 56 increases until the water leaks or seeps thought the article 50 as shown in FIG. 1B. Thus, the greater the height of the column of water or fluid that the fabric can hold, the greater the hydrostatic head and water resistance of the article.

One method of testing the hydrostatic pressure of a fabric is the American Association of Textile Chemists and Colorists ("AATCC") Test Method 127-2008. Testing the hydrostatic pressure of an article under the AATCC standard is completed either a hydrostatic pressure tester or a hydrostatic head tester. Using either of the aforementioned testers, which are described in further detail below, a minimum of three article specimens are taken diagonally across the width of the article to be representative of the material. The three specimens are cut to at least 200 millimeters×200 millimeters and handled as little as possible to avoid folding or contaminating the area to be tested. In testing an absorbent article using the aforementioned testers, water in a lower reservoir of the tester is at a temperature range of 65 degrees Fahrenheit to 75 degrees Fahrenheit. The surface of the specimen to be tested is clamped into the tester so that it faces the waterOnce the tester is activated, the hydrostatic pressure is recorded as soon as water droplets penetrate the article in three different places. The process is repeated for each sample and the average hydrostatic pressure is calculated for each sample. There was no screen used to back the samples.

One example of a hydrostatic head tester is the TEXTEST FX3000 Hydrostatic Head Tester "Hydrotester III" available from Benninger Corp., P.O. Box 1071, 885 Simuel Rd., Spartanburg, SC 29301. The TEXTEST FX3000 uses an electronically controlled pump to apply selectable hydrostatic pressure up to 60 millibars per minute to the bottom side of the article. A reservoir with a circular area of 95 to 105 centimeters squared (approximately 4.5 inches in diameter) contains distilled water which is applied to the article surface. The article is secured with a coaxial clamp which is equipped with viewing lamps to aid the operator In seeing the penetration of water droplets. A digital readout displays the pressure. Other types of hydrostatic pressure testers for measuring hydrostatic pressure in accordance with the aforementioned AATCC Test Method 127-2008 are listed online at http://www.aatcc.org/bg "AATC Buyer's Guide."

Hydrostatic pressure, which may be provided in millibars by the aforementioned tester may be converted to height of water in centimeters by multiplying the number of millibars by 1.02. Thus, the height C of water in centimeters ("cm") that corresponds with a pressure reading of M millibars ("mbar") may be expressed by the following equation:

$$C = M \times 1.02. \qquad \text{Equation 1}$$

Further, hydrostatic pressure may also be expressed as pounds per square inch ("psi") by the following equation:

$$P = \frac{D}{LVX} \times C, \qquad \text{Equation 2}$$

where P is pressure in pounds per square inch (psi), D is 62.4 pounds per cubic foot, L is 2.45 centimeters per inch, V is 1728 cubic inches per cubic foot, C is height in centimeters.

Air Permeability Testing

Figure 4:
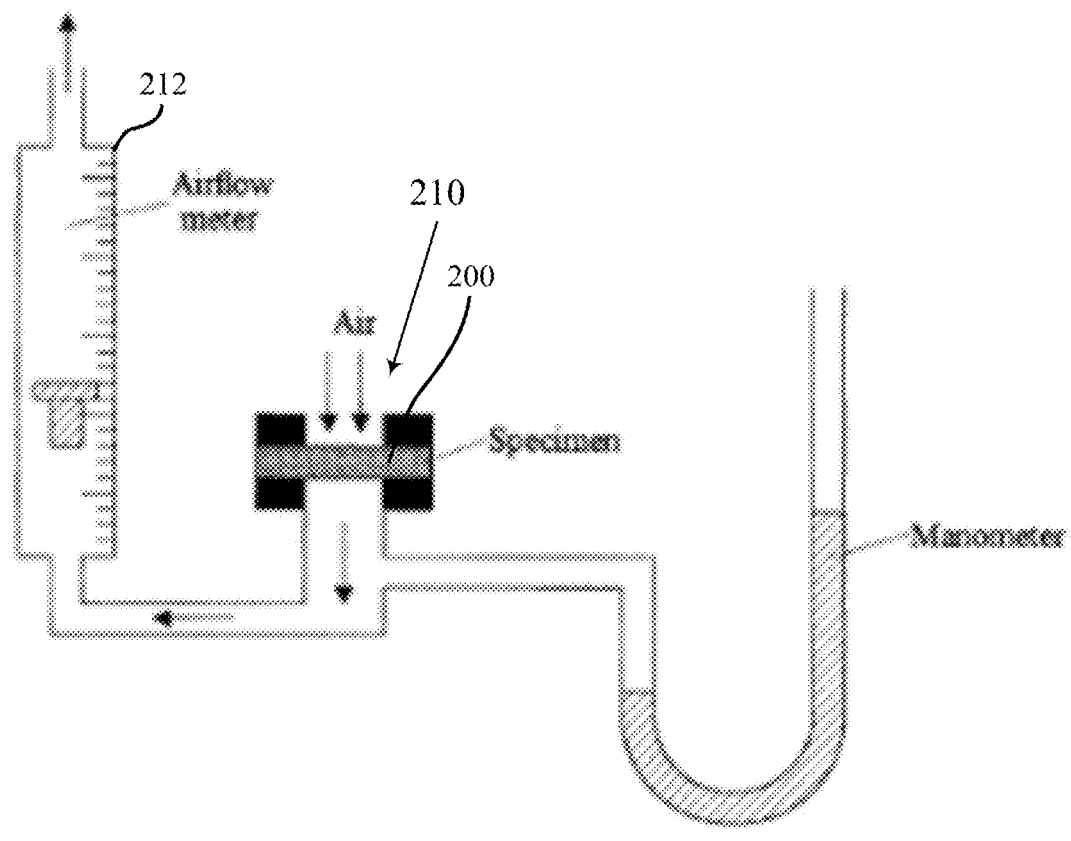
FIG. 4 is a diagram view of a related art air permeability test.

Air permeability is one indicator of breathability of water resistant or articles. FIG. 4 shows one simplified example of an air permeability test. Airflow through a given area of an article 200 is measured at a constant pressure drop across the article 200. The article 200 is clamped over an air inlet 210, and air is drawn through the article 200 by a suction pump (not shown). The rate of air flow is measured using a flow meter 212. Once a pressure difference of between the outer surface and inner surface of the article 200 is established, the air permeability can be calculated based on the flow rate of air and the area of the article 200.

American Society for Testing and Materials ("ASTM") D737-96, describes one example of a suitable protocol for measuring the air permeability of articles. The testing protocol requires an air permeability testing apparatus with a test head with an area of 38.0 centimeters squared to 38.6 centimeters squared. The testing apparatus draws air perpendicularly though the article that is clamped in the test head and allows adjustment for airflow rate for pressure differentials between 100 and 2500 pascals. At a minimum the test apparatus must provide a pressure differential of 125 pascals across the article.

One example testing apparatus is the TEXTEST FX 3300 Air permeability Tester III by Instruments AG, Dubendorfstrasse, 4 CH-8051 Zurich, Switzerland. In using the aforementioned apparatus to determine air permeability of an article, samples of the article that are 8 inches by 8 inches are cut and minimally handled to prevent any creasing or contamination. The test pressure was set to 125 pascals and units were set to cubic feet per minute. Each test specimen was clamped within the test head of the device. Once testing commences, the aforementioned apparatus provides a color range indicator when test is most accurate at which point measurements are recorded. An average of several samples of the same article is calculated and the table 2 and 3 provided under ASTM D737-96 is referenced to assure that the differences in values do not exceed the single-operator precision values provided in the aforementioned tables.

Countertop/Hard Surface Testing Procedure

As mentioned above, one method of testing the afore-mentioned incontinence pad or underpad is the countertop/hard surface test. It is noted that while an incontinence pad, underpad, or sheet is referenced when describing the coun-tertop/hard surface testing procedure, the disclosure and testing procedure is not limited to any specific article. The Countertop/Hard surface test is designed to test the perfor-mance of an article in a standardized way.

In performing the countertop/hard surface test, a solution of 0.9% Sodium Chloride (NaCl) solution is prepared and warmed to 90-100 degrees Fahrenheit. A single layer of forming tissue (the type of tissue that is used for airlaid core manufacturing) was pre-weighted and placed between a hard, flat surface, and the article to be tested with the insult side of the article facing upwards and away from the tissue. A dosing tube was centered over the center of the article to be tested and 1000 milliliters of the solution was provided to the dosing tube at 7 milliliters per second. The solution was allowed to absorb into the article for 1-minute. A 3.5 inch diameter cylindrical weight was placed in the middle of the insulted area. In the example testing in FIG. 2A, a 10 pound weight was used for 1 pounds per square inch testing and a 20 pound weight was provided for 2 pounds per square inch testing. After 10 minutes, the respective weigh was removed from the article and the tissue beneath the article was visually inspected for strikethrough. The strikethrough per-formance was marked as pass/fail dependent on if visible strikethrough, beyond condensation, was noted. The tissue was then weighed and the weight subtracted from the dry weight to determine weight gain. This testing was repeated multiple times for each sample, and an average weight gain, standard deviation, and maximum weight gain was recorded for each article.

Bed Testing Procedure

As mentioned above, one example of the disclosed article is an incontinence pad or sheet which may be used to absorb or isolate a mattress or other surface from any insult received on the insult side of the incontinence pad. It is noted that while an incontinence pad or sheet is referenced when describing the bed testing procedure, the disclosure and bed testing procedure is not limited to any specific article. The bed testing procedure is designed to test the performance of an article in a simulated real-world conditions. Thus, in addition to testing the hydrostatic pressure of an article a bed testing procedure is disclosed which was used to determine the ability of an article to resist moisture or water when used as an incontinence underpad for a patient. In the example test, a signal pad was placed under the non-insult side of the article in order to provide visualization of any leakage through the article. The signal pad and article were placed on a hospital bed with the insult side of the article facing upwards towards (i.e., towards a patient). A pre-set amount of blue dyed saline (e.g., 250 milliliters heated to a tem-perature of 90 to 100 degrees Fahrenheit) was placed on the insult side of the article using a 7 ml/sec flow rate. One minute after any puddles of liquid were absorbed by the insult side of the article, a thin film was placed over the insulted underpad and a patient (a person approximately 6 feet tall and 184 pounds) would lie down on the insult side of the article for 20 seconds. The patient would then roll over on their left side for 10 seconds and on their right side for 10 seconds. Then the patient would sit up and hold their head and legs up in the air for 20 more seconds. After the aforementioned steps were completed the patient would get off of the article. The pre-weighed marker pad would then be inspected for any signs of strikethrough of the saline. In addition, the signal pad would be weighed to determine the weight gain of saline that leaked from the non-insult side of the article into the marker pad. The weight gain included weight gain from condensation (not visible) and liquid strike through (blue dye visible).

Initial simulated use bed strikethrough testing, as shown in FIG. 2B was focused on a single 500 ml insult because that normally is the worst case scenario for strike through. 500 ml is more than twice the normal volume of a typical human adult insult. When an absorbent SAP containing core is insulted the fluff pulp rapidly acquires the saline as the liquid spreads out through capillary action. It takes 10 minutes or more for the SAP to fully swell as it absorbs the saline from the fluff pulp and the interstitial spaces. After 30 minutes fluid that is absorbed by the SAP absorption is completed. Fluid retention of fluff pulp is much lower than SAP fluid retention. Fluff pulp only cores have very low liquid retention In most cases. Whereas cores that contain both fluff pulp and SAP have much better fluid retention because the SAP locks in the fluid lowering the amount of fluid in the fluff pulp, improving the core liquid retention. FIG. 2B shows the result of the single insult testing. In addition, hard surface strike through testing using was conducted using 3.5 inch diameter cylindrical weights on a countertop using a 1000 ml insult and 1 minute weight time after the saline pond was absorbed into the core before applying the weight, These results are shown in FIG. 2C, none of the samples tested using the hard surface strike through testing showed liquid strike through at 1 or 2 psi during the countertop/hard surface testing.

During testing 500 ml of insult was divided into two 250 ml insults spread apart by 30 minutes. It was observed that in many cases the strike through performance of an absor-bent article subject to the aforementioned steps would appear satisfactory when the aforementioned steps were completed for the first time but would be greatly reduced once a second pre-set amount of saline was added to the article and the aforementioned steps were repeated, the example results of which are shown in FIG. 2C. Thus, the bed testing procedure was updated to repeat the aforemen-tioned procedure on each article 30 minutes after the first set of steps were completed.

The foregoing description of various aspects and examples have been presented for purposes of illustration and description. It is not intended to be exhaustive nor to limit the disclosure to the forms described. The embodiment(s) illustrated in the figures can, in some instances, be understood to be shown to scale for illustrative purposes. Numerous modifications are possible in light of the above teachings, including a combination of the above-mentioned aspects. Some of those modifications have been discussed and others will be understood by those skilled in the art. The various aspects were chosen and described in order to best illustrate the principles of the present disclosure and various aspects as are suited to the particular use contemplated. The scope of the present disclosure is, of course, not limited to the examples or aspects set forth herein, but can be employed in any number of applications and equivalent devices by those of ordinary skill in the art. Rather, it is hereby intended the scope be defined by the claims appended hereto.

What is claimed is:

1. An air-permeable absorbent underpad usable with a low-airloss-bed and configured to prevent liquid from passing from a first side of the absorbent underpad to a second side of the absorbent underpad, the underpad comprising:

a topsheet layer;

an absorbent core comprising fibers or a superabsorbent polymer; and a non-woven substrate backsheet comprising:

a first layer of spunbond fibers;

a second layer of spunbond fibers;

a first layer of meltblown fibers;

a second layer of meltblown fibers;

a third layer of meltblown fibers; and a fourth layer of meltblown fibers, wherein at least one of the layers of the non-woven substrate backsheet is treated with a fluorocarbon, and wherein the underpad is configured to cover at least a portion of the low-airloss-bed with the second side of the underpad facing a surface of the low-airloss-bed, and the substrate backsheet is configured to prevent liquid absorbed by the absorbent core of the underpad from passing to the second side of the underpad and to the surface of the low-airloss-bed, and wherein a hydrostatic pressure of the substrate backsheet is greater than or equal to 60 centimeters and less than or equal to 190 centimeters based on the American Association of Textile Chemists and Colorists (AATCC) Test Method 127-2008 and wherein an air permeability of the substrate backsheet is greater than or equal to 5 cubic feet per minute and less than or equal to 35 cubic feet per minute based on the American Society for Testing and Materials (ASTM D737-18) Standard Test Method for Air Permeability of Textile Fabrics.

2. The air-permeable absorbent underpad of claim 1, wherein the first layer of meltblown fibers, the second layer of meltblown fibers, the third layer of meltblown fibers, and the fourth layer of meltblown fibers are between the first layer of spunbond fibers and the second layer of spunbond fibers.

3. The air-permeable absorbent underpad of claim 1, wherein a hydrostatic pressure of the substrate backsheet ranges from 75-170 centimeters based on the American Association of Textile Chemists and Colorists (AATCC) Test Method 127-2008.

4. The air-permeable absorbent underpad of claim 1, wherein the hydrostatic pressure of the substrate backsheet ranges from 105 centimeters to 190 centimeters based on the American Association of Textile Chemists and Colorists (AATCC) Test Method 127-2008.

5. The air-permeable absorbent underpad of claim 1, wherein the substrate backsheet comprises a plurality non-woven substrates.

6. The air-permeable absorbent underpad of claim 1, wherein absorbent core comprises a superabsorbent polymer comprising a natural or synthetic polymer with a chemically bonded hydrophilic groups or polymer selected from the group comprising a sodium neutralized cross-linked poly-acrylate or polysaccharides.

7. The air-permeable absorbent underpad of claim 1, wherein an air permeability of the backsheet ranges from 10 to 35 cubic feet per minute based on the American Society for Testing and Materials (ASTM D737-18) Standard Test Method for Air Permeability of Textile Fabrics.

8. The air-permeable absorbent underpad of claim 1, wherein the absorbent core comprises fibers selected from a group comprising, fluff pulp, super absorbent fibers, cellulose acetate fibers, rayon fibers, LYOCELL fibers, polyacrylonitrile fibers, cotton fibers or cotton linter fibers, thermal bonding fibers including polypropylene, polyethylene/poly-propylene core sheath, polyester/polypropylene core sheath, or polyester/polyethylene core/sheath.

9. The air-permeable absorbent underpad of claim 1, wherein the core comprises a fiber and a super absorbent polymer.

10. The air-permeable absorbent underpad of claim 1, wherein the non-woven backsheet does not contain a porous film.

11. The air-permeable absorbent underpad of claim 1, wherein the non-woven backsheet has an alcohol repellency AR rating of between about 6 and 8 according to Nonwovens Standard Procedures ("NWSP") NWSP 080.8.RO.

12. The air-permeable absorbent underpad of claim 1, wherein the non-woven backsheet has an alcohol repellency AR rating of between about 7 and 8 according to Nonwovens Standard Procedures ("NWSP") NWSP 080.8 RO.

13. The air-permeable absorbent underpad of claim 1, wherein the underpad does not contain a microporous film.

14. An air-permeable absorbent underpad configured to prevent liquid from passing from a first side of the absorbent underpad to a second side of the absorbent underpad, the underpad comprising:

a topsheet layer;

an absorbent core comprising fibers or a superabsorbent polymer; and a non-woven backsheet comprising:

a first layer of spunbond fibers;

a second layer of spunbond fibers;

a first layer of meltblown fibers;

a second layer of meltblown fibers;

a third layer of meltblown fibers; and a fourth layer of meltblown fibers, wherein at least one of the layers of the non-woven backsheet is treated with a fluorocarbon, and the non-woven backsheet is configured to prevent liquid absorbed by the absorbent core of the underpad from passing through to the second side of the underpad, and wherein a hydrostatic pressure of the non-woven backsheet is greater than or equal to 60 centimeters and less than or equal to 190 centimeters based on the American Association of Textile Chemists and Colorists (AATCC) Test Method 127-2008, and wherein an air permeability of the non-woven backsheet is greater than or equal to 5 cubic feet per minute and less than or equal to 35 cubic feet per minute based on the American Society for Testing and Materials (ASTM D737-18) Standard Test Method for Air Permeability of Textile Fabrics.

15. The air-permeable absorbent underpad of claim 14, wherein the underpad does not contain a microporous film.

16. A system comprising a low-airloss-bed and an absorbent, air-permeable liquid barrier between a patient and the low-airloss-bed, the system further comprising:

a topsheet layer;

an absorbent core comprising fibers or a superabsorbent polymer; and a backsheet comprising:

a first layer of spunbond fibers;

a second layer of spunbond fibers;

a first layer of meltblown fibers;

a second layer of meltblown fibers;

a third layer of meltblown fibers; and a fourth layer of meltblown fibers, wherein at least one of the layers of the backsheet is treated with a fluorocarbon, and wherein the topsheet layer, the absorbent core, and the backsheet are configured to cover at least a portion of the low-airloss-bed and the backsheet is configured to provide a liquid resistant barrier between the absorbent core and the low-airloss-bed while allowing air from the low-airloss-bed to pass through the non-woven substrate, wherein a hydrostatic pressure of the backsheet is greater than or equal to 60 centimeters and less than or equal to 190 centimeters based on the American Association of Textile Chemists and Colorists (AATCC) Test Method 127-2008, and wherein an air permeability of the backsheet is greater than or equal to 5 cubic feet per minute and less than or equal to 35 cubic feet per minute based on the American Society for Testing and Materials (ASTM D737-18) Standard Test Method for Air Permeability of Textile Fabrics.

17. The system of claim 16, wherein the topsheet, absorbent core, and the backsheet do not contain a porous film.

18. The system of claim 16, wherein the backsheet does not contain a porous film.

19. The system of claim 16, wherein the air-permeable liquid barrier does not contain a microporous film.

* * * * *